United States Patent [19]
Cullinan et al.

[11] Patent Number: 5,843,940
[45] Date of Patent: Dec. 1, 1998

[54] BENZOTHIOPHENE COMPOUNDS, COMPOSITIONS, AND METHOD

[75] Inventors: George Joseph Cullinan, Trafalgar; Brian Stephen Muehl, Indianapolis, both of Ind.

[73] Assignee: Eli Lilly and Company, Indianapolis, Ind.

[21] Appl. No.: 957,004

[22] Filed: Oct. 23, 1997

Related U.S. Application Data

[60] Provisional application No. 60/029,050 Oct. 24, 1996.

[51] Int. Cl.$^6$ .......................... A61K 31/38; A61K 31/40; A61K 31/445; A61K 31/535
[52] U.S. Cl. ................. 514/212; 514/233.5; 514/324; 514/422; 514/443; 540/596; 544/145; 544/146; 546/202; 548/525; 549/51; 549/58
[58] Field of Search ............................ 540/596; 544/145, 544/146; 546/202; 548/525; 549/51, 58; 514/212, 233.5, 324, 422, 443

[56] References Cited

U.S. PATENT DOCUMENTS

| | | | |
|---|---|---|---|
| 3,274,213 | 9/1966 | Lednicer et al. | 548/576 |
| 3,394,125 | 7/1968 | Crenshaw | 578/525 |
| 3,413,305 | 11/1968 | Crenshaw | 548/525 |
| 4,133,814 | 1/1979 | Jones et al. | 260/326 |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones et al. | 546/237 |
| 5,147,880 | 9/1992 | Jones et al. | 514/650 |
| 5,395,842 | 3/1995 | Labrie | 514/320 |
| 5,470,854 | 11/1995 | Angerer et al. | 514/233 |
| 5,472,962 | 12/1995 | Koizumi et al. | 514/233.5 |
| 5,484,795 | 1/1996 | Bryant et al. | 514/212 |

FOREIGN PATENT DOCUMENTS

| | | |
|---|---|---|
| 062 503 | 10/1982 | European Pat. Off. . |
| WO 89/0289 | 4/1989 | WIPO . |
| WO 95/10513 | 4/1995 | WIPO . |

OTHER PUBLICATIONS

Crenshaw, R.R., et al, *J. Med. Chem.* 14 (12) :1185–1190 (1971).
Jones, C.D., et al, *J. Med. Chem.* 27 1057–1066 (1984).
Jones, C.D., et al, *J. Med. Chem.* 35: 931–938 (1992).

*Primary Examiner*—Richard L. Raymond
*Attorney, Agent, or Firm*—Janelle D. Strode; David E. Boone

[57] ABSTRACT

The invention provides benzothiophene compounds, formulations, and methods of inhibiting bone loss or bone resorption, particularly osteoporosis, and cardiovascular-related pathological conditions including hyperlipidemia, and estrogen-dependent cancer.

6 Claims, No Drawings

BENZOTHIOPHENE COMPOUNDS, COMPOSITIONS, AND METHOD

BACKGROUND OF THE INVENTION

This application claims the benefit of U.S. provisional application Ser. No. 60/029,050, filed Oct. 24, 1996.

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

Estrogen dependent cancers are major diseases effecting both women, and to a lesser extent men. Cancer cells of this type are dependent on a source of estrogen to maintain the orginal tumor as well as to proliferate and metastasize to other locations. The most common forms of estrogen dependent cancer are breast and uterine carcinomas. Current chemotherapy of these diseases relies primarily on the use of anti-estrogens, predominately tamoxifen. The use of tamoxifen, although efficaceous, is not without undesirable side-effects, for example, estrogen agonist properties, such as uterine hypertrophy and carcinogenic potential. Compounds of the current invention while showing the same or better potential for anti-cancer activity, also demonstrate a lower potential for estrogen agonist activity.

In response to the clear need for new pharmaceutical agents which are capable of alleviating the symptoms described herein, the instant invention provides benzo[b]thiophene compounds, pharmaceutical formulations, and methods of using said compounds for the inhibition of the disease states as indicated herein.

SUMMARY OF THE INVENTION

The instant invention relates to compounds of formula I:

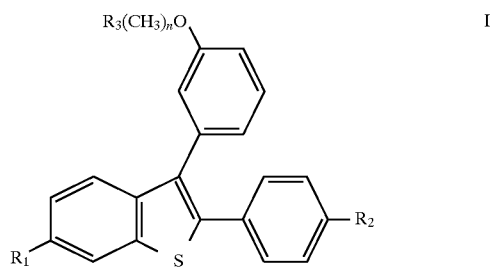

wherein:

$R^1$ is —H, —OH, —O($C_1$-$C_4$ alkyl), —OCO($C_1$-$C_6$ alkyl), —O(CO)O($C_1$-$C_6$ alkyl), —OCOAr, —O(CO)OAr, where Ar is phenyl or optionally substituted phenyl, or —OSO$_2$($C_2$-$C_6$ alkyl);

$R^2$ is —H, —OH, —O($C_1$-$C_4$ alkyl), —OCO($C_1$-$C_6$ alkyl), —O(CO)O($C_1$-$C_6$ alkyl), —OCOAr, —O(CO)OAr, where Ar is phenyl or optionally substituted phenyl, —OSO$_2$($C_2$-$C_6$ alkyl), —Cl, or —F;

$R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; and n is 2, 3, or 4;
or a pharmaceutically acceptable salt or solvate thereof.

The instant invention further provides pharmaceutical formulations containing compounds of formula I, and the use of said compounds at least for the inhibition of bone loss or bone resorption, particularly osteoporosis, and cardiovascular-related pathological conditions, including hyperlipidemia, and estrogen-dependent cancer.

DETAILED DESCRIPTION OF THE INVENTION

General terms used in the description of compounds herein described bear their usual meanings. For example, "$C_1$–$C_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like. Similarly, the term "—$OC_1$–$C_4$ alkyl" represents a $C_1$–$C_4$ alkyl group attached through an oxygen such as, for example, methoxy, ethoxy, n-propoxy, isopropoxy, and the like. Of these $C_1$–$C_4$ alkoxy groups, methoxy is highly preferred.

The term "substituted phenyl" refers to a phenyl group having one or more substituents selected from the group consisting of $C_1$–$C_4$ alkyl, —$OC_1$–$C_4$ alkyl, hydroxy, nitro, chloro, fluoro, or tri(chloro or fluoro)methyl.

The term "hydroxy protecting group" contemplates numerous functionalities used in the literature to protect a hydroxyl function during a chemical sequence and which can be removed to yield the phenol. Included within this group are acyls, mesylates, tosylates, benzyl, alkylsilyloxys, $C_1$–$C_4$ alkyls, and the like. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for removing preferred hydroxy protecting groups, particularly methyl, are essentially as described in the Examples, infra.

The term "leaving group" means a chemical entity which is capable of being displaced by an amino function via an $SN_2$ reaction. Such reactions are well known in the art and such groups would include halogens, mesylates, tosylates, and the like. A preferred leaving group is bromo.

The term "inhibit" includes its generally accepted meaning which includes prohibiting, preventing, restraining, and slowing, stopping, or reversing progression, severity, or ameliorating a resultant symptom or effect.

The term "solvate" represents an aggregate that comprises one or more molecules of the solute, such as a formula I compound, with one or more molecules of solvent.

The compounds of formula I are derivatives of benzo[b] thiophene which is named and numbered according to the Ring Index, The American Chemical Society, as follows:

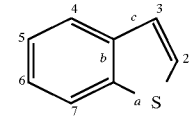

Compounds of formula I include:
2-(4-Methoxyphenyl)-3-[3-[2-(1-piperidinyl)ethoxy] phenyl]-6-methoxybenzo[b]thiophene hydrochloride;
2-(4-Methoxyphenyl)-3-[3-[3-(1-piperidinyl)propoxy] phenyl]-6-methoxybenzo[b]thiophene hydrochloride;
2-(4-Methoxyphenyl)-3-[3-[4-(1-piperidinyl)butoxy] phenyl]-6-methoxybenzo[b]thiophene hydrochloride;
2-(4—Hydroxyphenyl)-3-[3-[2-(1-piperidinyl)ethoxy] phenyl]-6-hydroxybenzo[b]thiophene hydrochloride;
2-(4—Hydroxyphenyl)-3-[3-(1-piperidinyl)propoxy] phenyl]-6-hydroxybenzo[b]thiophene;
2-(4—Hydroxyphenyl)-3-[3-(1-piperidinyl)butoxy]phenyl]-6-hydroxybenzo[b]thiophene hydrochloride;
2-(4-Methoxyphenyl)-3-[3-[2-(1-pyrrolidinyl)ethoxy] phenyl]-6-methoxybenzo[b]thiophene hydrochloride;
2-(4-Methoxyphenyl)-3-[3-[3-(1-pyrrolidinyl)propoxy] phenyl]-6-methoxybenzo[b]thiophene hydrochloride;
2-(4-Methoxyphenyl)-3-[3-[4-(1-pyrrolidinyl)butoxy] phenyl]-6-methoxybenzo[b]thiophene hydrochloride;
2-(4-Hydroxyphenyl)-3-[3-[2-(1-pyrrolidinyl)ethoxy] phenyl]-6-hydroxybenzo[b]thiophene hydrochloride;
2-(4-Hydroxyphenyl)-3-[3-(1-pyrrolidinyl)propoxy]phenyl] -6-hydroxybenzo[b]thiophene;
2-(4-Hydroxyphenyl)-3-[3-(1-pyrrolidinyl)butoxy]phenyl]-6-hydroxybenzo[b]thiophene hydrochloride; and the like.

Preferred embodiments of the current invention are those compounds wherein n is three and $R_3$ is piperidinyl.

Several synthetic pathways are available for preparing the compounds of the instant invention. One synthetic route is illustrated in Scheme I, below.

Scheme I

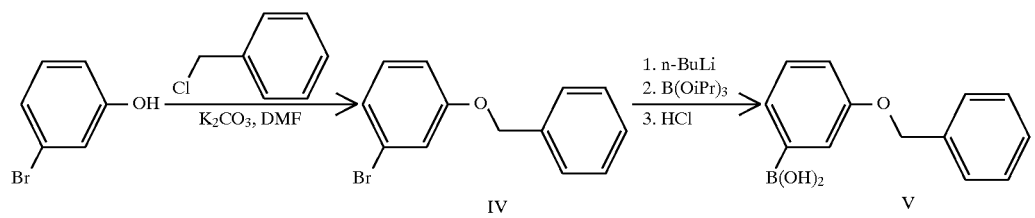

+

-continued
Scheme I

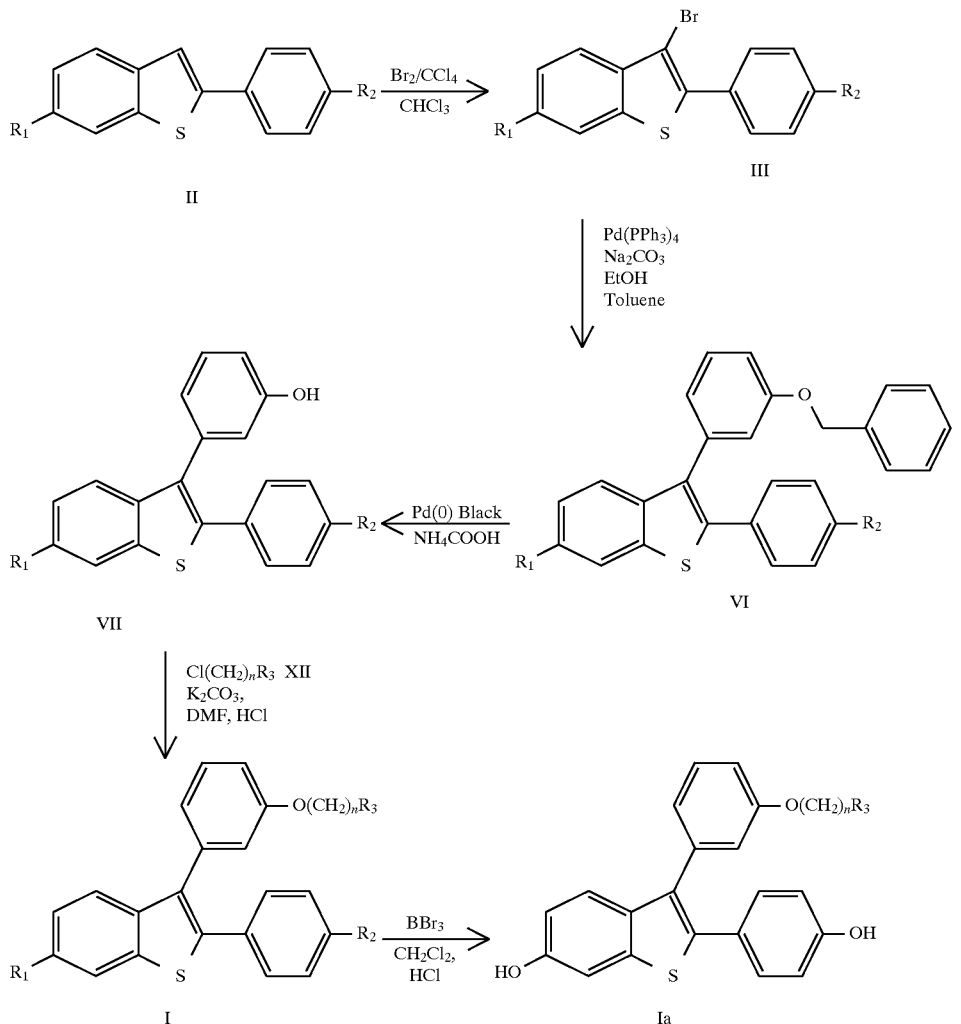

In the processes for preparing compounds of the present invention, the starting material for the benzo[b]thiophene derivatives are benzo[b]thiophene precursors of formula II:

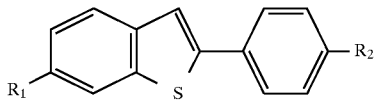

wherein $R_1$ and $R_2$ have their previous meanings.

A compound of formula II may be prepared in accordance with the methods in Jones et al., U.S. Pat. No. 4,133,814, the disclosure of which is herein incorporated by reference.

A compound of formula II is brominated with one equivalent of bromine in a suitable chlorinated solvent, such as chloroform, carbon tetrachloride, or mixtures thereof. The substrate is heated in the solvent to reflux. The bromine is added dropwise as the reaction is slowly cooled to room temperature to give a compound of formula III, which is brominated at the 3-position:

wherein $R_1$ and $R_2$ have their previous meanings.

Benzyl chloride and m-bromophenol are coupled in DMF with excess potassium carbonate overnight at room temperature to give a benzyl-protected phenolic compound of formula IV.

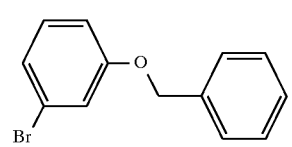

The benzyl protecting group is one of many groups which may be used to protect the phenol during the subsequent coupling reaction. See, for example, J. W. Barton, "Protective Groups in Organic Chemistry";, J. G. W. McOmie (ed.), Plenum Press, New York, N.Y., 1973, Chapter 2, and T. W.

Green, "Protective Groups in Organic Synthesis", John Wiley and Sons, New York, N.Y., 1981, Chapter 7.

The 3-benzyloxybromobenzene of formula IV is converted to the boronic acid derivative by dissolving in THF and adding one equivalent of n-butyllithium at −78° C. After stirring at −78° C. for approximately 30 minutes, one equivalent of triisopropyl borate is added and the reaction is slowly warmed to room temperature, followed by acidification with aqueous hydrochloric acid to give a 3-benzyloxybenzene boronic acid compound of formula V.

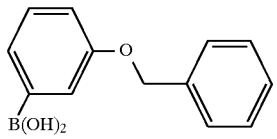

V

A compound of formula III and a compound of formula V are then combined in 10% ethanol in toluene with aqueous sodium carbonate and catalytic tetrakis(triphenylphosphine) palladium (0) and heated to reflux for 2–3 hours. Conventional thin layer chromatography is typically used to monitor the completion of the reaction, which yields a compound of formula VI.

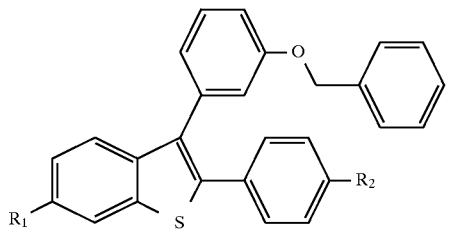

VI wherein $R_1$ and $R_2$ have their previous meanings.

The benzyloxy protecting group on a compound of formula VI may be removed by any of the available standard methods, such as hydrogenation, using catalytic palladium on activated carbon in THF, under pressure. Alternatively, the deprotection may be performed by refluxing for 30 minutes in an ethyl acetate/ethanol/water solvent system with one equivalent of palladium (0) black and five equivalents of ammonium formate giving the phenolic compound of formula VII. (See, for example, J. W. Barton, ibid.)

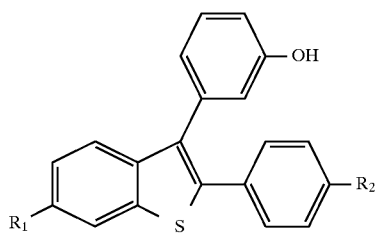

VII wherein $R_1$ and $R_2$ are as previously defined.

The phenolic compounds of formula VII derived above may be alkylated by adding a compound of formula XII in DMF at room temperature, usually overnight with an excess of dry potassium carbonate:

XII wherein $R_3$ and n have their previous meanings.

Alternately, the above phenol may be alkylated with an excess of a di-haloalkyl moiety to yield an oxy-alkyl-halo derivative, for example, a compound of formula XIII. Preferred halogens would be chloro or bromo, with bromo being particularly preferred.

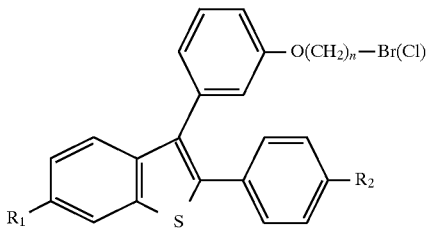

XIII wherein $R_1$, $R_2$, and n are as previously defined.

A compound of formula XIII may be converted to a compound of formula I by displacing the halogen with an appropriate amine in the presence of an inorganic base such as $K_2CO_3$ or the like. Compounds of formula I wherein $R_1$ and $R_2$ are esters or sulfonates may be derived from demethylating the mono- or di-methoxy compounds with $AlCl_3$, $BCl_3$, and the like, and acylating with the appropriate acyl or sulfonyl moiety. The methoxy groups are removed using an appropriate protocol, such that cleavage of the oxy-alkyl-base side-chain does not occur. This may be accomplished by converting the basic nitrogen to its hydrochloride salt.

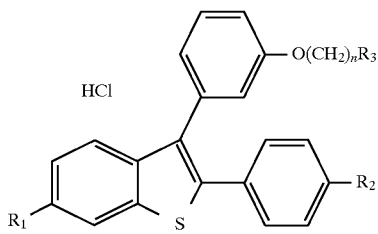

I wherein $R_1$, $R_2$, $R_3$, and n are as previously defined.

In the case where n is 4 in a compound of formula Ib, an alternate synthetic approach is taken, as 1-(4-chlorobutyl) piperidine hydrochloride is not readily available. A compound of formula VII is alkylated with 1,4-dibromobutane with excess dry potassium carbonate in 2-butanone at reflux for one hour, resulting in a compound of formula IX.

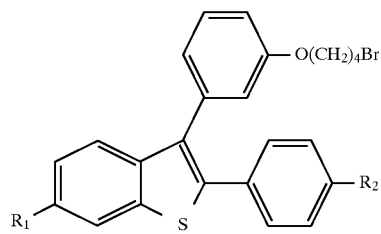

IX wherein $R_1$ and $R_2$ are as previously defined.

A compound of formula IX is then reacted with the appropriate base, such as for example piperidine, and excess dry potassium carbonate in DMF at reflux for 3 hours giving a compound of formula Ib. The HCl salt is made using standard techniques.

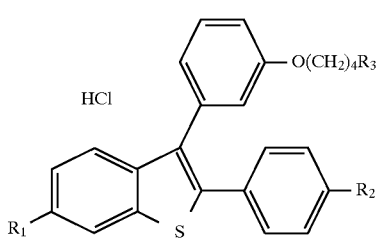

wherein $R_1$, $R_2$, and $R_3$ are as previously defined.

A compound of formula I wherein $R_1$ and $R_2$ are both —$OCH_3$ may be demethylated by reacting with 2.5 equivalents of boron tribromide in dichloromethane at 0° C. for 3 hours to provide compounds of formula Ia. The HCl salt is made by standard techniques.

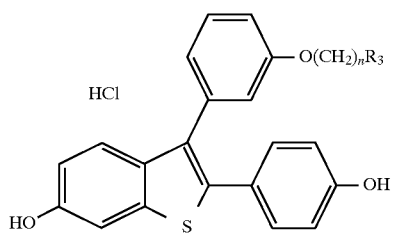

Compounds of formula Ia and Ib are encompassed by and included in the definition of a compound of formula I.

Although the free-base form of formula I compounds can be used in the methods of the instant invention, it is preferred to prepare and use a pharmaceutically acceptable salt form. The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The instant invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the instant invention which is capable of inhibiting, alleviating, ameliorating, treating, or preventing further symptoms in mammals, including humans, suffering from bone loss or bone resorption, particularly osteoporosis, and cardiovascular-related pathological conditions, including hyperlipidemia.

In the case of estrogen-dependent cancers, the term "effective amount" means the amount of compound of the instant invention which is capable of alleviating, ameliorating, inhibiting cancer growth, treating, or preventing the cancer and/or its symptoms in mammals, including humans.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to inhibit the symptoms and/or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg, one to three times per day. Such dosages will be administered to a patient in need thereof for at least one month, or more typically for six months, or chronically.

The instant invention also provides methods for inhibiting estrogen deficient pathologies including, for example, lack of birth control, postmenopausal syndrome including, for example, osteoporosis, cardiovascular disease, restenosis, and hyperlipidemia, certain cancers in men such as protate cancer, acne, hirsutism, dysfunctional uterine bleeding, dysmenorrhea, and atrophic vaginitis comprising administering to a mammal in need of treatment an effective amount of a compound of formula I, and, optionally, an effective amount of a progestin. One of skill in the art will recognize that estrogenic agents have a multitude of applications for treating estrogen deficient pathologies well beyond those listed, infra. The instant invention contemplates and encompasses such maladies although not specified by name.

The formulations which follow are given for purposes of illustration and are not intended to be limiting in any way. The total active ingredients in such formulations comprises from 0.1% to 99.9% by weight of the formulation. The term "active ingredient" means a compound of formula I.

Formulation 1: Gelatin Capsules

| Ingredient | Quantity (mg/capsule) |
|---|---|
| Active Ingredient | 0.1–1000 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

Formulation 2: Tablets

| Ingredient | Quantity (mg/tablet) |
|---|---|
| Active Ingredient | 2.5–1000 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50°–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

Formulation 3: Aerosol

| Ingredient | Weight % |
|---|---|
| Active Ingredient | 0.25 |
| Ethanol | 29.75 |
| Propellant 22 (Chlorodifluoromethane) | 70.00 |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Suppositories

| Ingredient | Weight |
|---|---|
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5: Suspension

Suspensions each containing 0.1–1000 mg of a compound of formula I per 5 mL dose.

| Ingredient | Weight |
|---|---|
| Active Ingredient | 0.1–1000 mg |
| Sodium carboxymethyl cellulose | 50 mg |
| Syrup | 1.25 mL |
| Benzoic acid solution (0.1M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following Preparations and Examples are provided to better elucidate the practice of the instant invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

NMR data for the following Examples were generated on a GE 300 MHz NMR instrument, and anhydrous $CDCl_3$ was used as the solvent unless otherwise indicated. Field strength for $^{13}C$ NMR spectra was 75.5 MHz, unless otherwise indicated.

EXAMPLES

Preparation 1

2-(4-Methoxyphenyl)-3-bromo-6-methoxybenzo[b] thiophene

A slurry of 2-(4-methoxyphenyl)-6-methoxybenzo[b] thiophene 100 g (370 mmol) in 1 L of $CHCl_3$ was heated to reflux then removed from the heat. A solution of 19.3 mL (370 mmol) of bromine in 170 mL of carbon tetrachloride was added dropwise as the solution slowly cooled to room temperature. The resulting mixture was concentrated to dryness in vacuo to yield 129 g of the title compound as brown solid.

PMR: Consistent with the proposed structure

MS: 348 and 350 (M+) FD

EA: Calc: C, 55.03; H, 3.75 Found: C, 55.30; H, 3.70 $C_{16}H_{13}BrO_2S$.

Preparation 2

3-Benzyloxy-bromobenzene

A slurry of 3-bromophenol 100 g (580 mmol), benzylchloride 80 g (700 mmol), and $K_2CO_{3\ 168}$ g (1210 mmol) in 2 L of DMF was stirred for sixteen hour at ambient temperature. The reaction mixture was filtered and evaporated to dryness. The solid was partioned between $CHCl_3$ and water. The organic layer was separated, washed twice with brine, and dried by filtration through anhydrous $Na_2SO_4$. The solution was evaporated to dryness. This yielded 142.5 g of the title compound as a white solid.

PMR: Consistent with the proposed structure

MS: 262 and 264 (M+) FD

EA: Calc: C, 59.34; H, 4.21 Found: C, 59.59; H, 4.17 $C_{13}H_{11}BrO$

Preparation 3

3-Benzyloxyphenyl Boronic Acid

A solution of 3-benzyloxy-bromobenzene 10 g (38 mmol) in 150 mL of anhydrous THF was cooled to −70° C. under a nitrogen atmosphere. 28.5 mL of n-butyl lithium (1.6M in hexanes) was added dropwise to the solution. The reaction mixture was stirred for 30 minutes, then tri-isopropyl borate 10.6 mL (45.6 mmol) was added. The reaction mixture was allowed to warm to ambient temperature over a two hour period. The reaction was quenched by the addition of 200 mL of 1N HCl and the reaction mixture was stirred for an additional hour. The slurry was extracted twice with EtOAc and the organic layer separated and combined. The EtOAc solution was washed twice with brine, dried with $Na_2SO_4$, and evaporated to a yellow oil. The product was crystallized from ether-hexane. This yielded 4.85 g of the title compound as white solid.

PMR: Consistent with the proposed structure.

Preparation 4

2-(4-Methoxyphenyl)-3-(3-benzyloxyphenyl)-6-methoxybenzo[b]thiophene

A solution of 2-(4-methoxyphenyl)-3-bromo-6-methoxybenzo[b]thiophene 40 g (112 mmol) and 3-benzyloxyphenyl boronic acid 51 g (224 mmol) in 1.4 L of toluene and 1 L of EtOH was prepared. To this solution was added a catalytic amount of tetrakis (triphenylphosphine)palladium (0) and 180 mL of 2N aqueous $Na_2CO_3$. The slurry was heated to reflux for one hour and allowed to cool. The organic layer was separated and washed twice with 0.1N NaOH, twice with brine, dried with $Na_2SO_4$, and evaporated to dryness. The product was chromatographed on a silica gel column eluted with a linear gradient begining with EtOAc-Hexane (9:1) (v/v) and ending with EtOAc-Hexane (4:1) (v/v). The desired fractions were determined by tlc, combined, and evaporated to a clear oil. This yielded 28 g of the title compound.

PMR: Consistent with the proposed structure

MS: m/e=452 (M+) FD

EA: Calc: C, 76.96; H, 5.35 Found: C, 76.75; H, 5.44 $C_{29}H_{24}O_3S$

Preparation 5

2-(4-Methoxyphenyl)-3-(3-hydroxyphenyl)-6-methoxybenzo[b]thiophene

A slurry was prepared consisting of 2-(4-methoxyphenyl)-3-(3-benzyloxyphenyl)-6-methoxybenzo[b]thiophene in 1 L of EtOH, 250 mL of EtOAc, and 40 mL of water. Palladium(0) black 4.04 g (38 mmol) and ammonium formate 12.6 g (200 mmol) was added. The reaction mixture was heated to reflux for one hour, then filtered hot through celite and evaporated to dryness. The solid was partioned between EtOAc and a saturated solution of $Na_2HCO_3$. The organic layer was washed with brine, dried with $Na_2SO_4$, and evaporated to dryness. This yielded 12.8 g of the title compound as a white solid.

PMR: Consistent with the proposed structure

MS: m/e=362 (M+) FD

EA: Calc: 72.90; H, 4.97 Found: C,73.11; H, 5.00 $C_{22}H_{18}O_3S$

Example 1

2-(4-Methoxyphenyl)-3-[3-[2-(1-piperidinyl)ethoxy] phenyl]-6-methoxybenzo[b]thiophene hydrochloride A slurry of 2-(4-Methoxyphenyl)-3-(3-hydroxyphenyl)-6-methoxybenzo[b]thiophene 2.7 g (7.1 mmol), 2-chloroethyl-piperidine hydrochloride 1.8 g (10.7 mmol), and $K_2CO_3$ 4.9 g (35.5 mmol) in 200 mL of DMF was prepared. The reaction was allowed to proceed for sixteen hours at ambient temperature. The reaction mixture was evaporated to dryness and the solid partitioned between EtOAc and water. The organic layer was separated and washed with brine and dried with $Na_2SO_4$. The solution was evaporated to a brown oil and re-dissolved in 80 mL of EtOAc. Dry HCl gas bubbled into the the EtOAc solution and a precipitate formed. The solvent was removed by evaporation. This yielded 2.8 g of the title compound as a tan powder.

PMR: Consistent with the proposed structure

MS: m/e=473 (M—HCl) FD

EA: Calc: C, 68.28; H, 6.32; N, 2.75 Found: C, 68.57; H, 6.23; N, 2.45 $C_{29}H_{32}ClNO_3S$

Example 2

2-(4-Methoxyphenyl)-3-[3-[3-(1-piperidinyl) propoxy]phenyl]-6-methoxybenzo[b]thiophene hydrochloride A manner similar to that used in Example 1, 3.09 g (8 mmol) of 2-(4-Methoxyphenyl)-3-(3-hydroxyphenyl)-6- methoxybenzo[b]thiophene, 2.4 g (12 mmol) of 1-(3-chloropropyl)piperidine hydrochloride, 5.5 g (40 mmol) of $K_2CO_3$ in 200 mL of DMF was coverted to 2.8 g of the title compound, isolated as a white solid.

PMR: Consistent with the proposed structure

MS: M/e=488 (M+) FD

EA: Calc: C, 68.75; H, 6.54; N, 2.67 Found: C, 68.49; H, 6.64; N, 2.81 $C_{30}H_{34}ClNO_3S$ Preparation 6

2-(4-Methoxyphenyl)-3-[3-(4-bromobutyl)phenyl]-6-methoxybenzo[b]thiophene

A slurry of 4.04 g (11 mmol) of 2-(4-Methoxyphenyl)-3-(3-hydroxyphenyl)-6-methoxybenzo[b]thiophene, 1,4-dibromobutane 26.3 mL (220 mmol), and 3.5 g (25.3 mmol) of $K_2CO_3$ in 200 mL of 2-butanone was preapared. The reaction mixture was heated to reflux for two hours, then filtered, and evaporated to dryness. The resulting oil was chromatographed on a silica gel column eluted with a linear gradient begining with EtOAc-hexane (1:9) (v/v) and ending with EtOAc-hexane (1:4) (v/v). The desired fractions were combined and evaporated to a yellow oil. This yielded 5 g of the title compound.

PMR: Consistent with the proposed structure

MS: m/e=497 and 499 (M+) FD

EA: Calc: C, 62.78; H, 5.07 Found: C, 62.59; H, 5.28 $C_{26}H_{25}BrNO_3S$

Example 3

2-(4-Methoxyphenyl)-3-[3-[4-(1-piperidinyl)butoxy]phenyl]-6-methoxybenzo[b]thiophene hydrochloride 2-(4-Methoxyphenyl)-3-[3-(4-bromobutyl)phenyl]-6-methoxybenzo[b]thiophene 5.4 g (11 mmol), 4.4 mL (44 mmol) of piperidine, and 6 g (44 mmol) of K2CO3 were added to 100 mL of DMF. The reaction mixture was heated to reflux for one hour, filtered, and evaporated to dryness. The resulting solid was partioned between EtOAc and water and the organic layer separated. The EtOAc solution was washed thrice with water, twice with brine, and dried with $Na_2SO_4$. The resulting solution was evaporated to a brown oil and redissolved in 80 mL of EtOAC. Dry HCl gas was bubled through the EtOAc solution and white precipitate formed. The solvent was removed by evaporation. This yielded 2.7 g of the title compound as a tan powder.

PMR: Consistent with the proposed structure

IR: (KBr) 3691, 3425, 2960, 2839, 2453, 2374,1603, 1577, 1542, 1508, 1473, 1439, 1352,1292, 1249, 1179, 1146, 1061, 1034, 832 $cm^{-1}$

HDMS: Calcd for $C_{31}H_{36}NO_3S$ (M-Cl): 502.2416 Fd: 502.2426

Example 4

2-(4—Hydroxyphenyl)-3-[3-[2-(1-piperidinyl)ethoxy]phenyl]-6-hydroxybenzo[b]thiophene hydrochloride 2-(4-Methoxyphenyl)-3-[3-[2-(1-piperidinyl)ethoxy]phenyl]-6-methoxybenzo[b]thiophene hydrochloride, 2 g (4 mmol) was dissolved in 125 mL of $CH_2Cl_2$ and cooled to 0+ C. 1.0 mL (10 mmol) of $BBr_3$ was added and the reaction mixture was stirred at 0° C. for 3 hours under a nitrogen atmosphere. The reaction was quenched by pouring into a mixture of 125 mL of aqueous $NaHCO_3$, 25 mL of isopropanol, and 250 mL of $CHCl_3$. The organic layer was separated and washed twice with brine, dried with $Na_2SO_4$, and evaporated to dryness. The resulting solid was re-dissolved in 150 mL of EtOAc and dry HCl gas was bubbled through. The solvents were removed by evaporation. This yielded 850 mg of the title compound as a white powder.

PMR: Consistent with the proposed structure

IR: (KBr) 3217, 2950, 2739, 1590, 1586, 1508, 1466, 1433, 1360,1262, 1216, 1171, 1148, 907 $cm^{-1}$

HRMS: Calcd. for $C_{27}H_{28}NO_3S$: 446.1790 Fd: 446.1795

Example 5

2-(4—Hydroxyphenyl)-3-[3-(1-piperidinyl)propoxy]phenyl]-6-hydroxybenzo[b]thiophene 1.1 g (2.1 mmol) of 2-(4-methoxyphenyl)-3-[3-[3-(1-piperidinyl)propoxy]phenyl]-6-methoxybenzo[b]thiophene hydrochloride was dissolved 60 mL of $CH_2Cl_2$ and cooled to 0° C. 0.5 mL (5.25 mmol) of $BBr_3$ was added and the reaction stirred for ninety minutes at 0° C. under a nitrogen atmosphere. The reaction was quenched by pouring it into a mixture of 125 mL of $NaHCO_3$, 25 mL of isopropanol, and 250 mL of $CHCl_3$. The organic layer was separated and washed twice with brine, dried with $Na_2SO_4$, and evaporated to dryness. The crude product was chromatographed on a silica gel column eluted with a linear gradient begining with $CHCl_3$ and ending with $CHCl_3$-MeOH (9:1) (v/v). The desired fractions were combined and evaporated to dryness. The hydrochloride salt was prepared as in Example 4. This yielded 550 mg of the title compound as a tan amorphous solid.

PMR: Consistent with the proposed structure.

MS: m/e=460 (M-Cl)

HRMS: Calcd. for $C_{28}H_{30}NO_3S$=460.1950 Fd: 460.1946

Example 6

2-(4—Hydroxyphenyl)-3-[3-(1-piperidinyl)butoxy]phenyl]-6-hydroxybenzo[b]thiophene hydrochloride In a manner similar to that of Example 4, 1.1 g (2.04 mmol) of 2-(4-methoxyphenyl)-3-[3-[4-(1-piperidinyl)butoxy]phenyl]-6-methoxybenzo[b]thiophene hydrochloride with 0.5 mL (5.1 mmol) of $BBr_3$ was converted to 370 mg of the title compound as a tan amorphous powder.

PMR: Consistent with the proposed structure

MS: m/e=473 (M+) FD

HRMS: Calcd. for $C_{29}H_{32}NO_3S$=474.2103 Fd: 474.2097

Test Procedures

In the examples illustrating the methods, a postmenopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection. After a one week acclimation period (therefore, two weeks post-OVX) daily dosing with test compound was initiated. 17α-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine:xylazine (2:1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis. Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve.

Uterine Eosinophil Peroxidase (EPO) Assay. Uteri were kept at 4° C. until time of enzymatic analysis. The uteri were then homogenized in 50 volumes of 50 mM Tris buffer (pH-8.0) containing 0.005% Triton X-100. Upon addition of 0.01% hydrogen peroxide and 10 mM O-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound: 17α-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below show comparative results among ovariectomized rats, rats treated with 17α-ethynyl estradiol ($EE_2$; an orally available form of estrogen), and rats treated with certain compounds of the instant invention. Although $EE_2$ caused a decrease in serum cholesterol when orally administered at 0.1 mg/kg/day, it also exerted a stimulatory action on the uterus so that $EE_2$ uterine weight was substantially greater than the uterine weight of ovariectomized test animals. This uterine response to estrogen is well recognized in the art.

Not only did the compounds of the instant invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the data below, estrogenicity also was assessed by evaluating the adverse response of eosinophil infiltration into the uterus. The compounds of the instant invention did not cause any increase in the number of eosinophils observed in the stromal layer of ovariectomized rats, while estradiol cause a substantial, expected increase in eosinophil infiltration.

The data presented in Table 1 below reflects the response of 5 to 6 rats per treatment.

TABLE 1

| Compound No. | Dose mg/kg[a] | Uterine Weight % Inc[b] | Uterine Eosinophil (Vmax)[c] | Serum Cholest. % Dec.[d] |
|---|---|---|---|---|
| EE2[e] | 0.1 | 118.6* | 234.2* | 89.3* |
| Ex 1 | 0.1 | 24 | 7.5 | 25.8 |
|  | 1.0 | 37.2* | 22.2 | 56.1* |
|  | 10.0 | 68.2* | 103.5* | 71.1* |
| Ex 2 | 0.1 | 20.2 | 24.0 | 59.1* |
|  | 1.0 | 35.7* | 32.4 | 76.5* |
|  | 10.0 | 39.1* | 32.1 | 69.4* |
| Ex 3 | 0.1 | 23.9 | 4.8 | 35.5* |
|  | 1.0 | 62.1* | 43.5* | 64.4* |
|  | 10.0 | 65.0* | −91.2* | 78.0* |
| Ex 4 | 0.1 | 9.1 | 4.8 | 33.3* |
|  | 1.0 | 5.6 | 4.8 | 57.2* |
|  | 10.0 | 78.7* | 103.8* | 81.0* |
| Compound A[f] | 0.1 | 24.6* | 21.0* | 45.4* |
|  | 1.0 | 64.8* | 49.9* | 68.8* |
|  | 10.0 | 41.7* | 55.9* | 65.3* |

[a]mg/kg PO
[b]Uterine Weight % increase versus the ovariectomized controls
[c]Eosinophil peroxidase Vmax
[d]Serum cholesterol decrease versus ovariectomized controls
[e]17-α-Ethynyl-estradiol
[f]2-(4-Hydroxyphenyl)-3-[4-[2-(1-piperidinyl)ethoxy]phenyl]-6-hydroxybenzo[b]thiophene (see: Crenshaw U.S. Pat. No. 3,413,305)
*p < .05

In addition to the demonstrated benefits of the compounds of the instant invention, the above data clearly demonstrate that compounds of Formula I are not estrogen mimetics. Furthermore, no deleterious toxicological effects (for example, survival numbers) were observed with any treatment.

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, compounds of the instant invention and ethynyl estradiol ($EE_2$) in 20% hydroxypropyl β-cyclodextrin are orally administered to test animals. Distal femur metaphysis and proximal tibiae data are compared to intact and ovariectomized test animals. Results are reported as percent protection relative to ovariectomy.

Ovariectomy of the test animals causes a significant reduction in femur density compared to intact, vehicle treated controls. Orally administered ethynyl estradiol ($EE_2$) prevents this loss, but the risk of uterine stimulation with this treatment is ever-present.

Estrogen Dependent Breast Cancer: MCF-7 Proliferation Assay Test Procedure

MCF-7 breast adenocarcinoma cells (ATCC HTB 22) are maintained in MEM (minimal essential medium, phenol-red free, Sigma St.Louis Mo.) supplimented with 10% fetal bovine serum (FBS) (v/v), L-glutamine (2 mM), sodium pyruvate (1 mM), HEPES (10 mM), non-essential amino acids and bovine insulin (1 ug/mL). Ten days prior to the assay, the MCF-7 cells are switched to maintenance medium supplemented with 10% dextrancoated charcoal stripped fetal bovine serum (DCC-FBS) assay medium in place of the 10% FBS to deplete internal stores of estrogen. MCF-7 cells are removed from the maintenance flasks using a cell dissociating medium (Ca/Mg free HBSS (phenol-red free) supplemented with 10 mM HEPES and 2 mM EDTA. Cells are washed twice with the assay medium and adjusted to 80,000 cells/mL. Approximately 100 mL (8,000 cells) are added to a flat-bottomed microculture well (Costar 3596) and incubated at 370° C. in a 5% $CO_2$ humidified incubator for 48 hours to allow cell adherence and equilibrium after transfer. Serial dilutions of the compounds of formula I or DMSO as a diluent control are prepared in assay medium and 50 mL transferred to triplicate microcultures followed by 50 mL of assay medium for a final volume of 200 mL. After an additional 48 hours of incubation, the microcultures are pulsed with tritiated thymidine (1 mCi/well) for 4 hours. Culture are terminated by freezing at −70° C. for 24 hours followed by thawing and harvesting of microcultures using a Skatron Semiautomatic Cell Harvester. Samples are counted by liquid scintillation. Fifty percent inhibitory concentration of the test drugs ($IC_{50}$) are determined versus the control (DMSO). Compounds of the present invention are active in this experimental model as seen below in Table 2.

TABLE 2

| Compound | $IC_{50}$ |
|---|---|
| 4 | 8 nN |
| 5 | 0.2 nM |
| 6 | 2 nM |

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenzo[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

We claim:

1. A method of inhibiting bone loss or bone resorption which comprises administering to a patient in need thereof an effective amount of a compound of formula I:

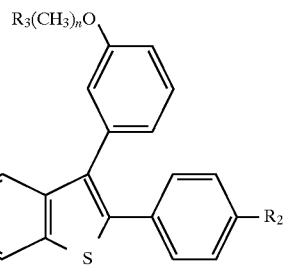

wherein:

$R^1$ is —H, —OH, —O($C_1$–$C_4$ alkyl), —OCO($C_1$–$C_6$ alkyl), —O(CO)O($C_1$–$C_6$ alkyl), —OCOAr, —O(CO)OAr, where Ar is phenyl or optionally substituted phenyl, or —OSO$_2$($C_2$–$C_6$ alkyl);

$R^2$ is —H, —OH, —O($C_1$–$C_4$ alkyl), —OCO($C_1$–$C_6$ alkyl), —O(CO)O($C_1$–$C_6$ alkyl), —OCOAr, —O(CO)OAr, where Ar is phenyl or optionally substituted phenyl, —OSO$_2$($C_2$–$C_6$ alkyl), —Cl, or —F;

$R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; and n is 2, 3, or 4;

or a pharmaceutically acceptable salt or solvate thereof.

2. A method according to claim 1, wherein said bone loss or bone resorption is due to menopause or ovariectomy.

3. A method of lowering serum cholesterol levels which comprises administering to a patient in need thereof an effective amount of a compound of formula I:

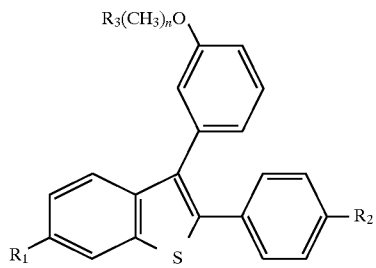

wherein:

$R^1$ is —H, —OH, —O($C_1$–$C_4$ alkyl), —OCO($C_1$–$C_6$ alkyl), —O(CO)O($C_1$–$C_6$ alkyl), —OCOAr, —O(CO)OAr, where Ar is phenyl or optionally substituted phenyl, or —OSO$_2$($C_2$–$C_6$ alkyl);

$R^2$ is —H, —OH, —O($C_1$–$C_4$ alkyl), —OCO($C_1$–$C_6$ alkyl), —O(CO)O($C_1$–$C_6$ alkyl), —OCOAr, —O(CO)OAr, where Ar is phenyl or optionally substituted phenyl, —OSO$_2$($C_2$–$C_6$ alkyl), —Cl, or —F;

$R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; and n is 2, 3, or 4;

or a pharmaceutically acceptable salt or solvate thereof.

4. A method of inhibiting estrogen-dependent cancer which comprises administering to a patient in need thereof an effective amount of a compound of formula I:

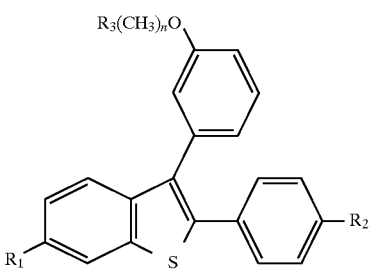

wherein:

$R^1$ is —H, —OH, —O($C_1$–$C_4$ alkyl), —OCO($C_1$–$C_6$ alkyl), —O(CO)O($C_1$–$C_6$ alkyl), —OCOAr, —O(CO)OAr, where Ar is phenyl or optionally substituted phenyl, or —OSO$_2$($C_2$–$C_6$ alkyl);

$R^2$ is —H, —OH, —O($C_1$–$C_4$ alkyl), —OCO($C_1$–$C_6$ alkyl), —O(CO)O($C_1$–$C_6$ alkyl), —OCOAr, —O(CO)OAr, where Ar is phenyl or optionally substituted phenyl, —OSO$_2$($C_2$–$C_6$ alkyl), —Cl, or —F;

$R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; and n is 2, 3, or 4;

or a pharmaceutically acceptable salt or solvate thereof.

5. A method according to claim 4 wherein said estrogen-dependent cancer is breast cancer.

6. A method according to claim 4 wherein said estrogen-dependent cancer is uterine cancer.

* * * * *

UNITED STATES PATENT AND TRADEMARK OFFICE
CERTIFICATE OF CORRECTION

PATENT NO. : 5,843,940

DATED : December 1, 1998

INVENTOR(S) :

George Joseph Cullinan and Brian Stephen Muehl

It is certified that error appears in the above-identified patent and that said Letters Patent is hereby corrected as shown below:

The structure of compounds of formula I, which appears in column 2, and in Claims 3 and 4 should have a $R_3(CH_2)_nO-$ moiety not $R_3(CH_3)_nO-$.

Signed and Sealed this

Twenty-fourth Day of August, 1999

Attest:

Q. TODD DICKINSON

*Attesting Officer*       *Acting Commissioner of Patents and Trademarks*